(12) United States Patent
Islava (10) Patent No.: US 10,092,194 B2
(45) Date of Patent: Oct. 9, 2018

(54) ILLUMINATED BLOOD PRESSURE CUFF

(71) Applicant: Care 2 Innovations, Inc., Newport Beach, CA (US)

(72) Inventor: Steve Islava, Newport Beach, CA (US)

(*) Notice: Subject to any disclaimer, the term of this patent is extended or adjusted under 35 U.S.C. 154(b) by 238 days.

(21) Appl. No.: 14/989,622

(22) Filed: Jan. 6, 2016

(65) Prior Publication Data

US 2017/0188857 A1  Jul. 6, 2017

(51) Int. Cl.
*G01L 7/00* (2006.01)
*A61B 5/021* (2006.01)
*G01L 9/16* (2006.01)

(52) U.S. Cl.
CPC .......... *A61B 5/02141* (2013.01); *G01L 9/16* (2013.01); *A61B 2560/0425* (2013.01)

(58) Field of Classification Search
None
See application file for complete search history.

(56) References Cited

U.S. PATENT DOCUMENTS

| | | |
|---|---|---|
| 2,761,056 A | 8/1956 | Lazo |
| 3,699,915 A | 10/1972 | Greene |
| 3,896,791 A | 7/1975 | Ono |
| 4,275,393 A | 6/1981 | Johnston |
| 4,300,548 A | 11/1981 | Jones |
| 4,417,586 A | 11/1983 | Jewett |
| 4,970,400 A | 11/1990 | Muramatsu |
| 5,050,527 A | 9/1991 | Kameda |
| 5,920,150 A | 7/1999 | Crary |
| 6,019,730 A | 2/2000 | Rashman |
| 6,206,533 B1 | 3/2001 | Shi |
| 6,415,672 B1* | 7/2002 | Hamilton ............... G01D 13/20 374/E1.018 |
| 6,481,291 B1* | 11/2002 | Lia .......................... A61B 5/021 73/715 |
| 7,716,990 B1 | 5/2010 | Sacerio |
| 8,474,321 B2 | 7/2013 | Seltzer |
| 2002/0005066 A1* | 1/2002 | Tanner .................... G01L 17/00 73/146 |
| 2002/0053236 A1* | 5/2002 | Hamilton ............... G01D 13/04 73/81 |

(Continued)

FOREIGN PATENT DOCUMENTS

JP  1130534  2/1999

*Primary Examiner* — Andre Allen
(74) *Attorney, Agent, or Firm* — Marcus C. Dawes; Daniel L. Dawes (57) ABSTRACT

A blood pressure gauge for monitoring the blood pressure values of a patient in a darkened or low light environment. The blood pressure gauge is selectively illuminated when an internal air pressure within an attached blood pressure cuff is first detected or after it has reached a predetermined threshold value as determined by a pressure transducer in the blood pressure gauge. The blood pressure gauge is illuminated by a plurality of light emitting diodes or by plurality of components comprised of photoluminescent material. The blood pressure cuff is inflated by the actuation of a bulb attached to the blood pressure gauge. The bulb is actuated or squeezed against a stationary hand grip portion of the blood pressure gauge so as to provide a greater compressive force and deliver a larger volume of air to the blood pressure cuff.

12 Claims, 8 Drawing Sheets

(56) References Cited

U.S. PATENT DOCUMENTS

| | | | |
|---|---|---|---|
| 2002/0121150 A1* | 9/2002 | Hamilton | G01D 13/20 73/866.3 |
| 2008/0002386 A1 | 1/2008 | Mezouari | |
| 2008/0074863 A1 | 3/2008 | Golle | |
| 2008/0271527 A1* | 11/2008 | Hewitt | G01F 23/164 73/299 |
| 2009/0044631 A1* | 2/2009 | Neighoff, Jr. | G01D 11/28 73/738 |
| 2009/0126482 A1 | 5/2009 | Fundak | |
| 2011/0271538 A1 | 11/2011 | Adachi | |

* cited by examiner

ILLUMINATED BLOOD PRESSURE CUFF

BACKGROUND

Field of the Technology

The disclosure relates to the field of emergency field medical devices, particularly to blood pressure cuffs or other blood pressure measuring devices.

Description of the Prior Art

Blood pressure cuffs and monitors have long been used to measure the relative blood pressure of a patient. The majority of blood pressure cuffs or monitors comprise an upper arm portion which fits around the bicep region of the patient. Other monitors comprise fingertip cuffs which attach to the individual fingers of the patient. Regardless of where the cuff attaches, once the cuff is in place, air is directed into the cuff which then begins to inflate. Many blood pressure cuffs are manual and require a user to pump air into the cuff via manipulation of a bulb or other pumping means. Still further blood pressure cuffs are automatic or are battery powered and send air into the cuff by operation of a small compression motor. As the cuff inflates, an increasing pressure is exerted on the patient until blood flow within the region of the attached cuff has stopped. Air is then slowly leaked out from the cuff until blood flow begins to return to the cuffed region, marking the value of the systolic pressure of the patient. The cuff continues to deflate until blood flow within the cuffed region returns to normal which then marks the diastolic pressure value of the patient. Using the obtained systolic and diastolic pressure values, along with a measured pulse or heart rate, a doctor, EMT, or other health care professional can have a quick basic snapshot of the one of the patient's most important biometric values, thus helping the health care professional diagnosis or treat the patient more effectively.

The problem with many blood pressure monitoring devices however is that they can be inefficient when inflating their respective cuff portions. In emergency situations, this is particularly relevant since time is of the essence and EMTs and other emergency personnel need as much medical information about the patient as soon as possible. Additionally, the EMT needs the results from the blood pressure monitoring device to be easily obtainable and legible in any environment the patient happens to be in so that the EMT has accurate medical information quickly regardless of the particular circumstances of the situation.

BRIEF SUMMARY

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
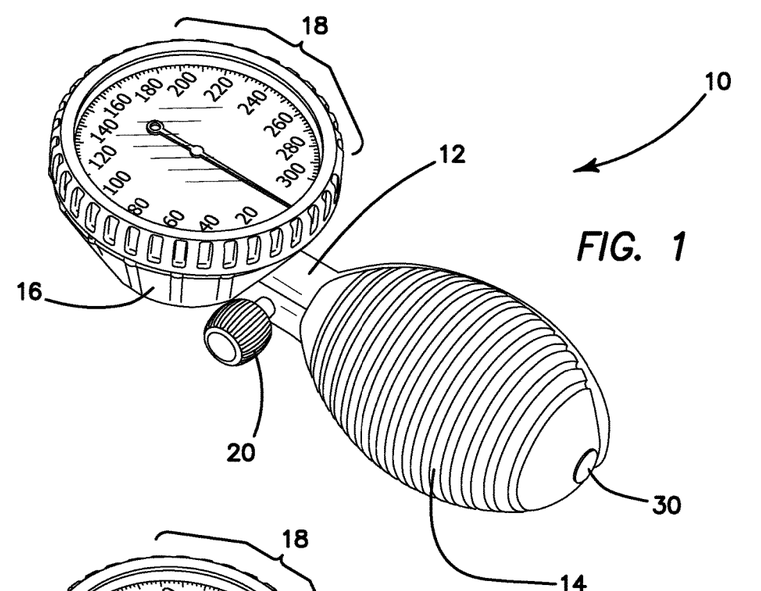
FIG. 1 is a perspective view of the blood pressure gauge of the current invention.

The current device is a blood pressure gauge and is shown in FIG. 1 and is generally denoted by reference numeral 10. The blood pressure gauge 10 comprises a body 12 with a bulb 14 coupled to its proximal end and a dial housing 16 coupled to its distal end. The dial housing 16 in turn comprises a dial assembly 18 which is detailed further below. Disposed on the body 12 between the bulb 14 and the dial housing 16 is a release valve 20.

Figure 2A:
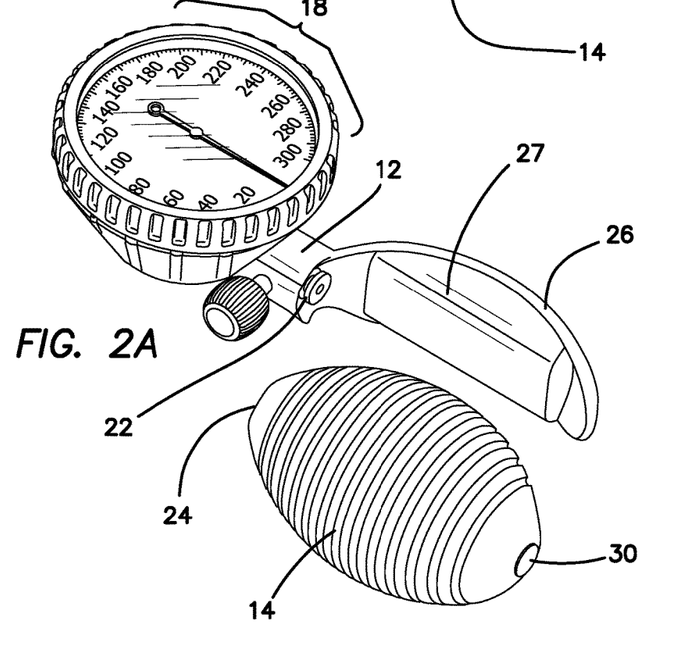
FIG. 2A is a perspective view of the blood pressure gauge seen in FIG. 1 with the bulb removed from a hand grip portion of the blood pressure gauge.
Figure 2B:
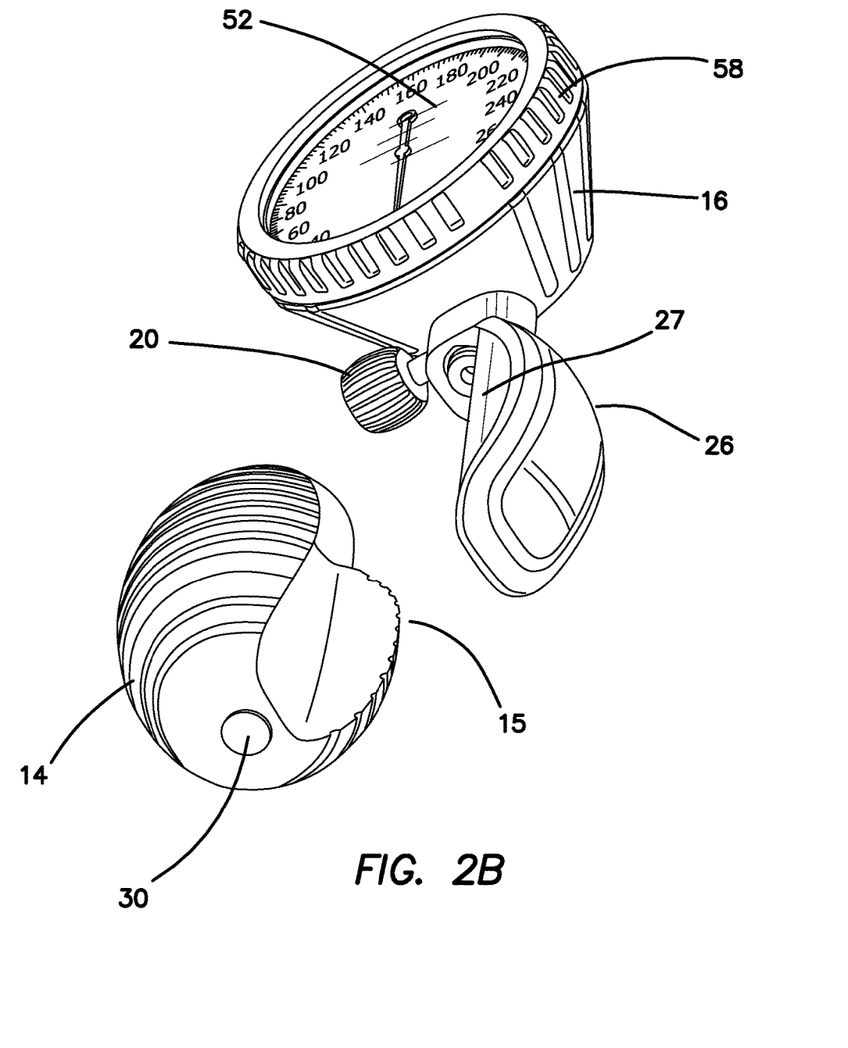
FIG. 2B is a rotated perspective view of the blood pressure gauge seen in FIG. 2A.

The bulb 14 is removably coupled to the body 12 via a connector 22 disposed within the body 12 itself as seen in FIG. 2A. A distal end 24 of the bulb 14 couples to the aperture 22 as is known in the art so that when air is expelled from the bulb 14, it enters the body 12 via the aperture 22. The bulb 14 further comprises an intake valve 30 in the proximal end of the bulb 14. As seen in FIG. 2A, disposed on a proximal portion of the body 12 is a substantially concave-shaped hand grip 26. The hand grip 26 is electronically coupled to the dial assembly 18 and comprises a concave shape or contour in order to accommodate the substantially oval or egg-shaped form of the bulb 14. On the inside surface of the hand grip 26 is a battery pack 27 as best seen in FIG. 2B which may house one or more portable or rechargeable batteries as are known in the art. FIG. 2B additionally shows where the bulb 14 comprises an indentation 15 defined in its surface which is shaped and configured to fully accommodate the battery pack 27 therein. The indentation 15 ensures that as the bulb 14 is squeezed as detailed further below, the battery pack 27 does not interfere with the movement of air entering and exiting the bulb 14. In addition to carrying a battery, the battery pack 27 may also accommodate various electronic components for the gauge 10 including but not limited to a microcontroller and a RAM or ROM memory chip.

In addition to help secure the bulb 14 in place within the body 12, the hand grip 26 provides a static or fixed backing for the bulb 14 as it is being squeezed or actuated by a user. Specifically, because the bulb 14 is compressed against a firm backing while it is being actuated, the user may apply a greater force to the bulb 14 than what would have been otherwise possible if no hand grip 26 had been present. See FIG. 3 which shows the direction in which a compressive force is applied to the bulb 14 by arrows 28. After squeezing the bulb 14, the user allows the bulb 14 to expand back into its original position by releasing the bulb 14. Air then rushes in through the intake valve 30 to refill the vacuum previously created by the compression of the bulb 14.

Figure 3:
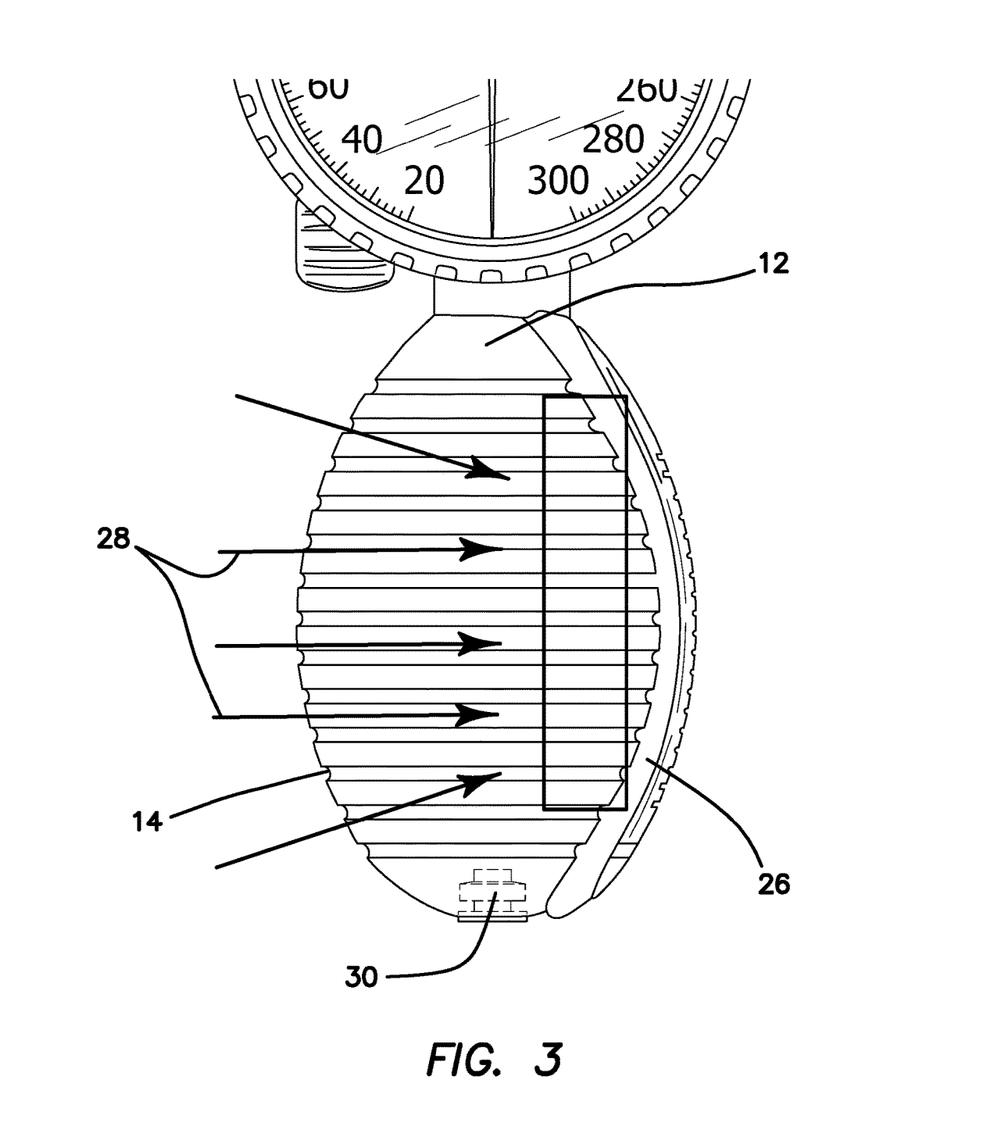
FIG. 3 is a magnified top down view of the blood pressure gauge.

Because a greater squeezing force is being applied to the bulb 14 due to the concave shaped hand grip 26, a larger volume of air originally contained within the bulb 14 is being directed out of the bulb's distal end 24 into the body 12 and then subsequently into the blood pressure cuff. With a larger volume of air being delivered to the blood pressure cuff with each squeeze of the bulb 14, the blood pressure cuff is inflated faster which in turn allows the gauge 10 to provide a blood pressure reading of the patient to the EMT or user in less time from what would have been required using a bulb without a rigid backing.

Figure 4:
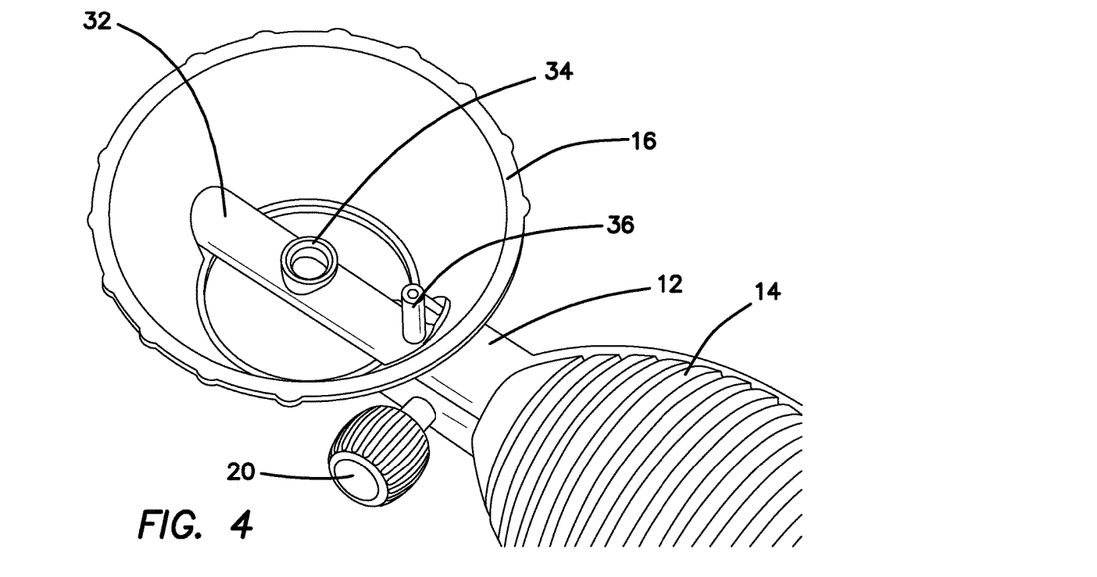
FIG. 4 is a perspective view of the blood pressure gauge seen in FIG. 1 with a dial assembly portion removed from the blood pressure gauge.

The body 12 of the gauge 10 serves as a conduit for air to be brought from the bulb 14 through the dial assembly 18 and into a standard or well known blood pressure cuff (not shown). Specifically, the body 12 directs air from the compressed bulb 14 into the dial housing 16 via a dial airway 32 disposed across the diameter of the dial housing 16 as seen in FIG. 4 where the dial assembly 18 has been removed from the housing 16. The dial airway 32 comprises a dial outlet 34 defined in its longitudinal center and a transducer outlet 36 disposed near the inner surface of the dial housing 16. The dial outlet 34 comprises a large circular opening defined in the surface of the dial airway 32. The transducer outlet 36 is a substantially cylindrical hollow tube orientated perpendicularly with respect to the dial airway 32. Both the dial outlet 34 and transducer outlet 36 communicate with the internal volume of the dial airway 32 and allow the passage of air there through, specifically as a volume of air is moving through the body 12, a portion of the air is diverted into the transducer outlet 36 while another portion of air is diverted through the dial outlet 34. The remainder of the incoming air moves through the remaining length of the airway 32 as detailed further below.

Figure 5:
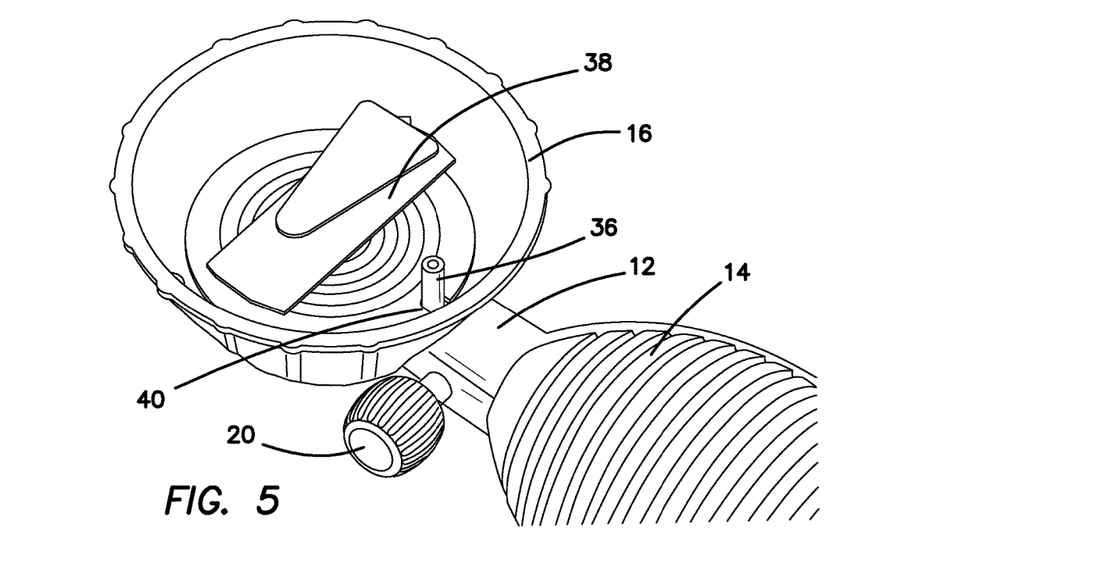
FIG. 5 is a perspective view of the blood pressure gauge seen in FIG. 4 with a gauge assembly disposed within a housing portion of the blood pressure gauge.

As seen in FIG. 5, a gauge assembly 38 is disposed within the housing 16. The gauge assembly 38 comprises all the necessary components commonly used within pressure gauges known within the art including but not limited to a pressure connection, a hair spring, a plurality of gears, a pinion, and/or a diaphragm. The pressure connection or pressure fitting (not seen) of the gauge assembly 38 couples to or otherwise engages with the dial outlet 34 so as to form an air tight or sealed fit as is known in the art. The gauge assembly 38 as a whole is nested within the housing 16 and comprises a notch 40 defined therein so that when the gauge assembly 38 is lowered into the dial outlet 34 of the airway 32, the notch 40 fits around the transducer outlet 36 so that the transducer outlet 36 extends above the gauge assembly 38 as seen in FIG. 5.

Figure 6:
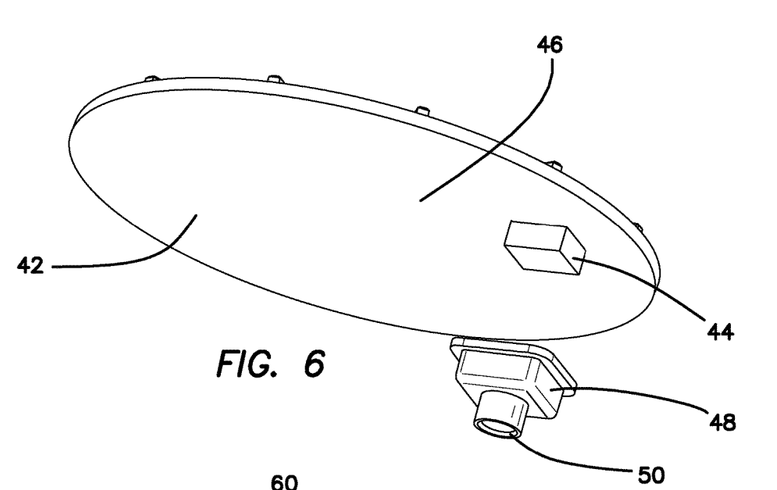
FIG. 6 is a partially exploded view of the back side of the dial portion of the blood pressure gauge seen in FIG. 1.
Figure 7:
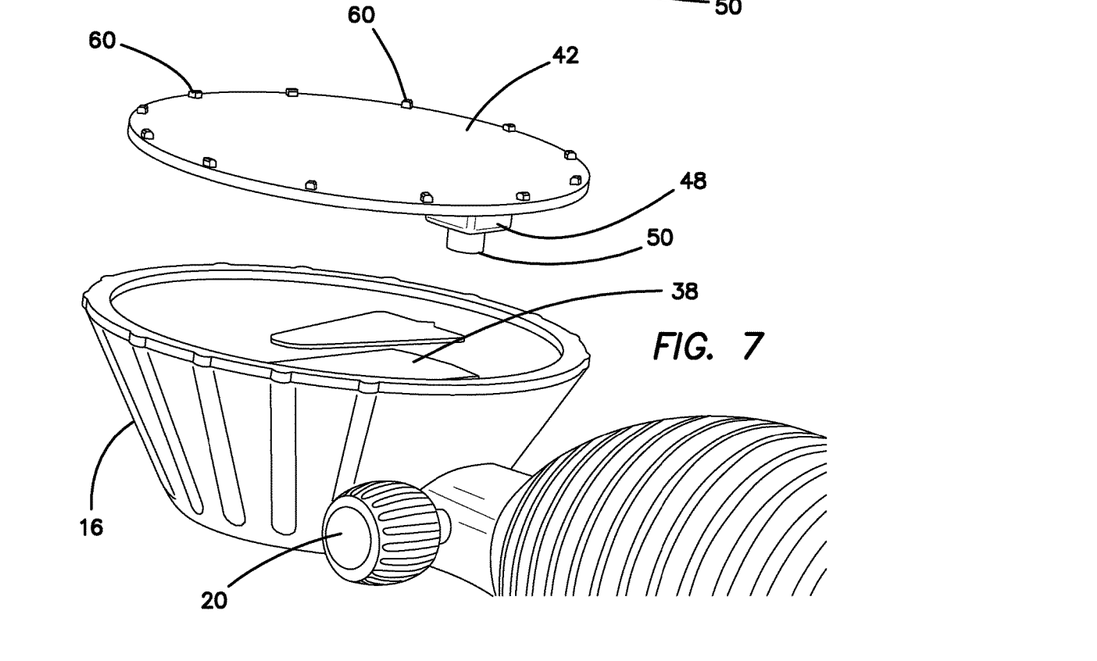
FIG. 7 is a partially exploded view of the blood pressure gauge seen in FIG. 1 with the dial removed from the dial assembly removed.

A partially exploded view of a dial 42 and a pressure transducer 44 used in the dial assembly 18 is seen in FIG. 6. Specifically, a pressure transducer 44 is coupled to the underside or bottom surface 46 of the dial 42. A molded cover 48 is also coupled to the bottom surface 46 which fits over transducer 44. The cover 48 comprises an aperture 50 which is orientated perpendicularly with respect to the bottom surface 46. The dial 42 is placed over the gauge assembly 38 as seen in FIG. 7, specifically with the end of the transducer outlet 36 being inserted into the aperture 50 of the cover 48. Air which is diverted into the transducer outlet 36 is then directed directly onto the pressure transducer 44 with the cover 48 effectively forming a seal over the pressure transducer 44 and preventing any air from escaping therefrom which thus ensures a more accurate reading of the incoming air by the pressure transducer 44. In addition to the transducer outlet 36 being coupled to the cover 48, the bottom surface 46 of the dial 42 is coupled to the gauge assembly 38 as is known in the art.

Figure 8:
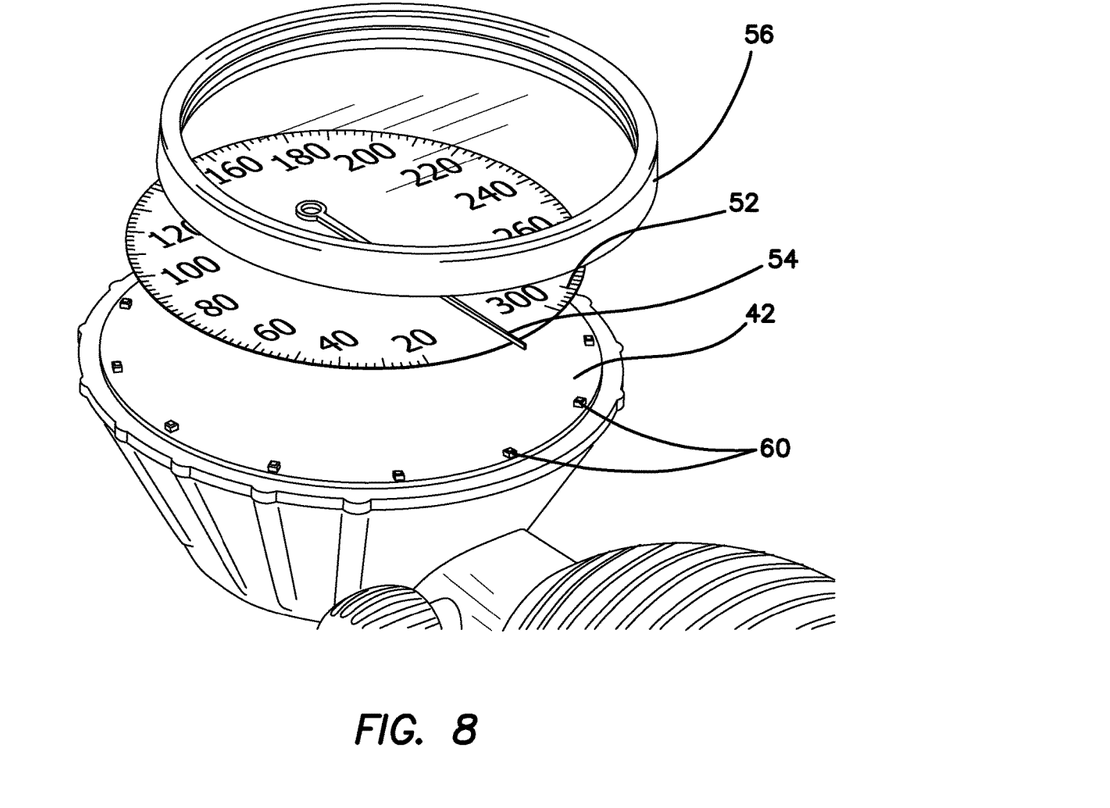
FIG. 8 is a partially exploded view of the components comprising the dial assembly portion of the blood pressure gauge seen in FIG. 1.
Figure 9:
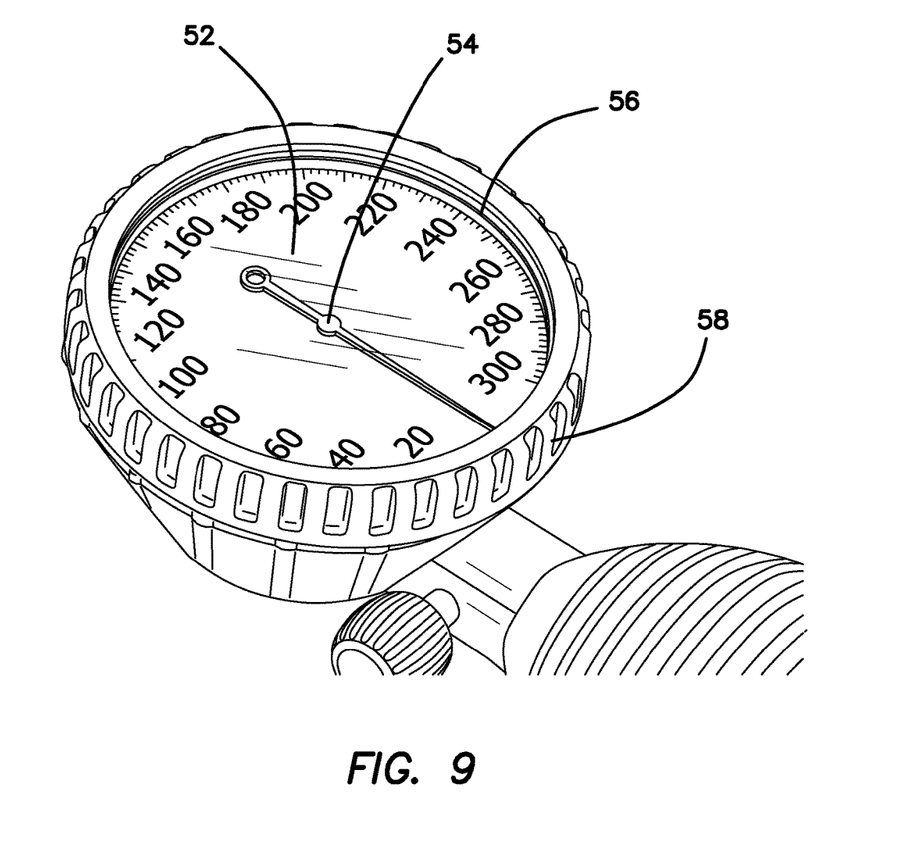
FIG. 9 is a magnified view of the dial assembly portion of the blood pressure gauge seen in FIG. 1.

Greater detail of the dial assembly 18 may be seen in FIGS. 8 and 9. Specifically, FIG. 8 shows a partially exploded view of the dial assembly 18 which comprises the dial 42, a dial face 52, a needle 54, and an illumination ring 56. FIG. 9 shows the dial assembly 18 after being coupled to the housing 16 with a cap 58 locking the remaining components of the dial assembly 18 into place within the housing 16. The dial assembly 18 may also further comprising a clear plastic or glass plate disposed in the cap 56 which covers and protects the dial 42 as is known in the art. The dial face 52, needle 54, and illumination ring 56 may be comprised of photoluminescent plastics or other material which comprises the ability to absorb ambient light and then emit the absorbed light later in a darkened environment. Alternatively, the illumination ring 56 may comprise an LED light strip disposed in its inner circumference, facing the dial face 52. However the preferred embodiment for providing illumination to the dial assembly 18 is provided by a plurality of LEDs 60 symmetrically disposed around the dial 42 as best seen in FIGS. 7 and 8. The LEDs 60 are electronically coupled to the pressure transducer 44 and to the gauge assembly 38 and are selectively activated as detailed further below.

The dial assembly 18 and the blood pressure gauge 10 as a whole may also comprise a number of conventional biometric sensors or other electronics without departing from the original spirit and scope of the invention. For example, the dial assembly may also comprise a wireless transmitter or receiver such as a Blue Tooth® antenna or other WiFi antenna. Additionally, accelerometers and gyroscopes as are known in the art can also be employed within the dial housing 16 which report the relative movement of the dial housing 16 and which may activate the means for illuminating the blood pressure gauge 10. The blood pressure gauge 10 may also comprise a suite of biometric sensors, either disposed within the dial assembly 18 or hand grip 26 directly, or coupled to the blood pressure gauge 10 by means known in the art. Such biometric sensors may include but are not limited to a heartrate monitor, an EMG sensor, a humidity sensor, a thermometer, and a fingerprint scanner. Furthermore, the blood pressure gauge 10 may also comprise a camera or camera sensor, as well as a RFID reader to be used in conjunction with other known medical devices in the treatment of the patient.

Figure 10:
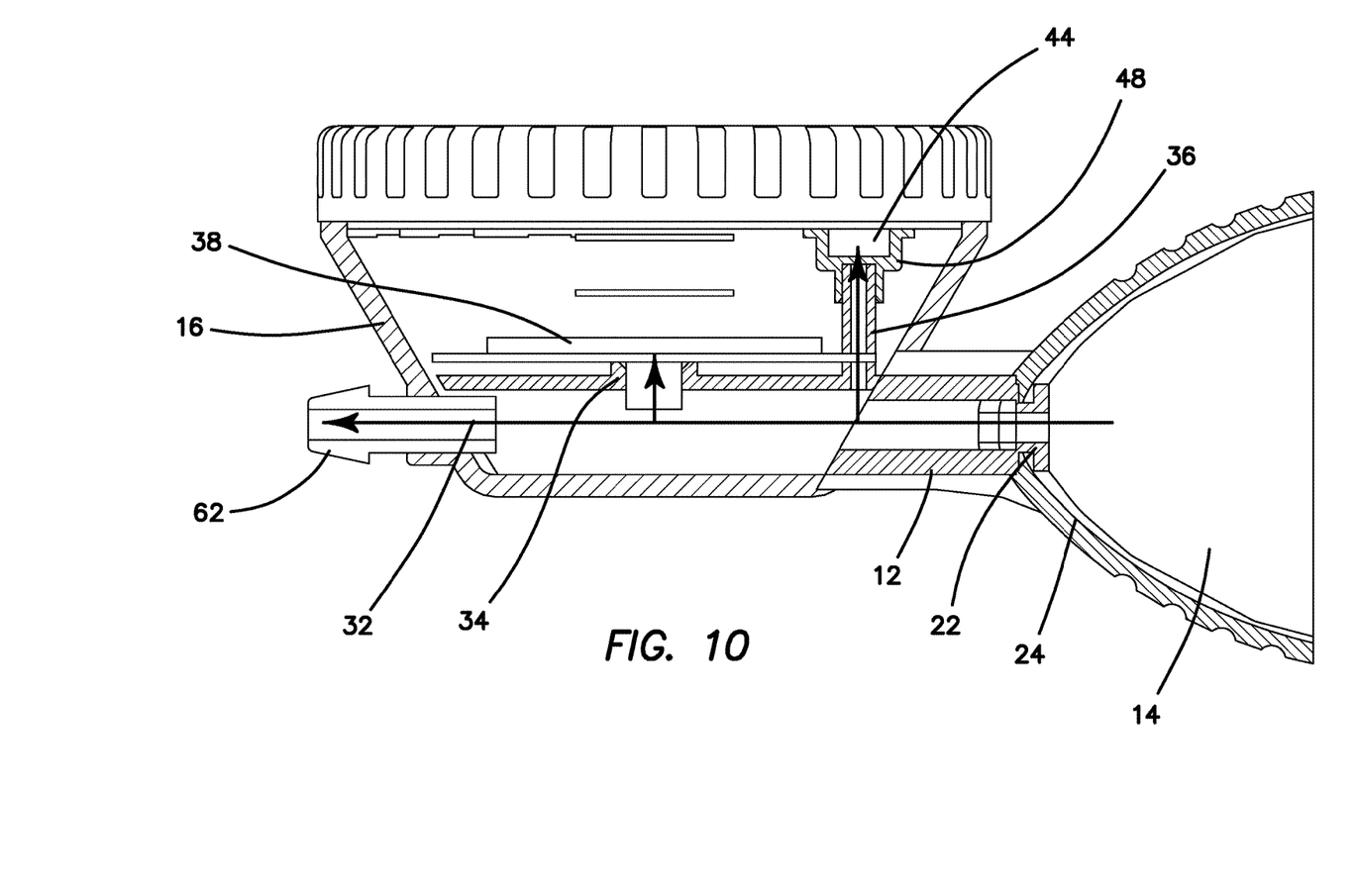
FIG. 10 is a side cross sectional view of the blood pressure gauge seen in FIG. 1.

Detail of the operation of the blood pressure gauge 10 may be seen in FIG. 10. When the bulb 14 is compressed, air within the bulb 14 is forced through the distal end 24 of the bulb 14 and into the body 12 of the gauge 10 via the connector 22. The air is then directed down the dial airway 32 which traverses the dial housing 16. The pressure of the incoming air through the airway 32 forces the air up through both the transducer outlet 36 and the dial outlet 34. Air entering the transducer outlet 36 enters the cover 48 via the aperture 50 and makes contact with the pressure transducer 44 disposed on the underside of the dial 42. Correspondingly, air directed upward through the dial outlet 34 makes contact with the gauge assembly 38. The remaining air from the bulb 14 continues to pass through the airway 32 and exits the blood pressure gauge 10 through a hose connector 62. Coupled to the hose connector 62 is a hose (not shown) which in turn is connected to a blood pressure cuff which is wrapped around or coupled to the patient as is known in the art.

Air which is compressed from the bulb 14 is replaced by ambient air that rushes into the bulb 14 through the intake valve 30 when the compression force applied to the bulb 14 is lessened. The bulb 14 is repeatedly compressed as needed and air is sent through the blood pressure gauge 10 and into the blood pressure cuff until the cuff begins to inflate. When the release valve 20 disposed in the body 12 is in a closed position, a closed system is created and air that has entered the cuff and blood pressure gauge 10 is prevented from back flowing into the bulb 14. As air is continually pumped through the blood pressure gauge 10 and into the cuff, the cuff inflates and the internal pressure within the blood pressure gauge 10 increases. This likewise increases the air pressure within the dial outlet 32 and transducer outlet 36 which in turn increases the air pressure on the gauge assembly 38 and pressure transducer 44, respectively.

The air against the gauge assembly 38 activates the components contained therein which in turn rotates the needle 54 to a corresponding measurement value given on the dial face 52 as is known in the art. At the same time, the air pressure is measured by the pressure transducer 44 and is converted into an electronic signal which may be used to illuminate the gauge 10. In one embodiment, as soon as the pressure transducer 44 detects a readable air pressure, the resulting signal is sent to the LEDs 60 disposed on the dial 42 which then illuminate the dial face 52 allowing the user to see the needle 54 and resulting pressure reading within the cuff is in a darkened environment. Alternatively, the signal may be sent to the LED strip disposed in the illumination ring 56, allowing for a border region surrounding the dial face 52 to be illuminated. In another embodiment, an electronic signal to illuminate the LEDs 60 or the illumination ring 56 may be generated by the pressure transducer 44 only after the pressure within the cuff has reached a predetermined threshold value. For example, the LEDs 60 may be illuminated only after the pressure within the attached cuff has reached 100 mmHg as determined by the pressure transducer 44, or alternatively, as determined by the gauge assembly 38. Similarly, the pressure transducer 44 may be configured to turn off the LEDs 60 when the pressure within the cuff has dropped below a certain predetermined value. For example, if the pressure within the attached cuff has drops below 20 mmHg as determined by the pressure transducer 44 or the gauge assembly 38, the LEDs 60 are switched off in order to preserve battery life among other considerations.

When the cuff coupled to the blood pressure gauge 10 is fully inflated by the actuation of the bulb 14, the pressure within the cuff stops the flow of blood traveling through the artery that the cuff is disposed around. The user then releases the air pressure within the cuff by turning the release valve 20 into the open position which allows the air within the cuff to escape into the ambient environment. As the air pressure within the cuff is reduced, blood flow begins to return the artery beneath the cuff. The user notes the reading on the dial face 52 at this point with the assistance of a stethoscope, the resulting reading being the systolic pressure of the patient. The user continues to allow the release of air from the cuff via the release valve 20 and monitor the dial face 52 until blood flow completely returns to the artery of the patient. The user then notes this second reading which represents the diastolic pressure of the patient. With the systolic and diastolic pressures of the patient determined, the user can then remove the blood pressure cuff and blood pressure gauge 10 and proceed with corresponding treatment, or alternatively, measure the patient's blood pressure values again if needed.

Many alterations and modifications may be made by those having ordinary skill in the art without departing from the spirit and scope of the embodiments. Therefore, it must be understood that the illustrated embodiment has been set forth only for the purposes of example and that it should not be taken as For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. An apparatus for measuring the blood pressure of a patient comprising:
   a body;
   a concave hand grip disposed at a proximal end of the body;
   a bulb coupled to the proximal end of the body and nested against the concave hand grip;
   a dial housing disposed on a distal end of the body; and
   a dial assembly coupled to the dial housing,
   wherein the dial assembly comprises a pressure transducer and an illumination source for selectively illuminating the dial assembly, and
   wherein the illumination source is configured to activate upon a threshold pressure being obtained as determined by the pressure transducer.

2. The apparatus of claim 1 where the body further comprises:
   a hose connector disposed at a distal end of the body;
   a dial airway coupling the hose connector at the distal end of the body with the bulb at the proximal end of the body;
   a dial outlet defined in the dial airway at an angle that is perpendicular relative to the dial airway; and
   a transducer outlet coupled to the dial airway at an angle that is perpendicular relative to the dial airway.

3. The apparatus of claim 2 further comprising a gauge assembly disposed in the dial housing, wherein the gauge assembly is coupled to the dial assembly and forms a sealed fit with the dial outlet defined in the dial airway.

4. The apparatus of claim 1 where the dial assembly comprises:
   a dial, the dial comprising a top surface and a bottom surface; and
   a dial face coupled to the top surface of the dial,
   wherein the pressure transducer is coupled to the bottom surface of the dial.

5. The apparatus of claim 4 where the illumination source for selectively illuminating the dial assembly is a plurality of light emitting diodes (LEDs) disposed on the top surface of the dial.

6. The apparatus of claim 5 where the plurality of LEDs disposed on the top surface of the dial are disposed symmetrically around the dial face coupled to the top surface of the dial.

7. The apparatus of claim 4 where the illumination source for selectively illuminating the dial assembly is an illumination ring disposed around the dial face coupled to the top surface of the dial.

8. The apparatus of claim 7 where the illumination ring and dial face are comprised of photoluminescent material.

9. The apparatus of claim 1 where the bulb comprises an indentation defined in its surface to accommodate the concave hand grip disposed at the proximal end of the body.

10. The apparatus of claim 1 wherein the concave hand grip comprises a battery pack.

11. The apparatus of claim 1 further comprising a release valve disposed in the body between the proximal end of the body and the dial housing.

12. The apparatus of claim 4 further comprising a cover disposed over the pressure transducer coupled to the bottom surface of the dial, the cover further forming a sealed coupling with the transducer outlet.

* * * * *